United States Patent [19]

Klimchak

[11] Patent Number: 4,744,907

[45] Date of Patent: May 17, 1988

[54] BLOOD CELL SEPARATION

[75] Inventor: Robert J. Klimchak, Flemington, N.J.

[73] Assignee: Interferon Sciences, Inc., New Brunswick, N.J.

[21] Appl. No.: 3,838

[22] Filed: Jan. 16, 1987

[51] Int. Cl.$^4$ ............................................. B01D 21/00
[52] U.S. Cl. .................................. 210/730; 210/789; 424/101; 436/177
[58] Field of Search ............... 210/730, 789, 800, 516, 210/725; 436/63, 177, 68; 424/101

[56] References Cited

U.S. PATENT DOCUMENTS

| 3,338,828 | 8/1967 | Clark | 210/730 |
| 4,255,256 | 3/1981 | Ferrante et al. | 210/730 |
| 4,487,700 | 12/1984 | Kanter | 210/789 |
| 4,589,987 | 5/1986 | Kenney | 210/730 |

FOREIGN PATENT DOCUMENTS

| 559303 | 6/1958 | Canada | 210/730 |
| 0036168 | 9/1981 | European Pat. Off. | 210/730 |

Primary Examiner—Benoit Castel
Attorney, Agent, or Firm—Irene J. Frangos; Vincent P. Pirri

[57] ABSTRACT

Hydroxyalkyl celluloses are useful as sedimenting agents in the non-destructive separation of red and white blood cells. Intact WBC recovery is higher than with conventional methods. The white blood cells may be used in interferon production.

12 Claims, No Drawings

BLOOD CELL SEPARATION

TECHNICAL FIELD OF THE INVENTION

This invention relates to the separation of leukocytes and erythrocytes by sedimentation at normal gravity in the presence of a hydroxyalkyl cellulose. More particularly, this invention refers to a method for recovering approximately 80% of the original leukocytes while leaving red blood cells intact. The leukocytes may be used in interferon production.

BACKGROUND OF THE INVENTION

Hydroxyethyl starch has routinely been used as a sedimenting agent [Lionetti, U.S. Pat. No. 4,004,975; Pestka, U.S. Pat. No. 4,289,690; Djerassi, U.S. Pat. No. 4,111,199; Chadha, U.S. Pat. No. 4,485,038; and Van Oss, et al., *Immunol. Commun.*, 10(6), pp. 549–55 (1981)]. Treatment with hydroxyethyl starch ("HES") results in recovery of about 68% of the original pool of leukocytes or white blood cells ("WBC"). Ammonium chloride lysis yields 90% of the WBCs, but is undesirable in view of the wasteful destruction of the red blood cells ("RBCs").

Other agents which have been used as sedimenting agents are Dextran (glucose polymer), Ficoll (sucrose polymer), PVP, fenugreek seed extract, and phytohemagglutinins [Lichtenstein, U.S. Pat. No. 3,709,791; Chany, U.S. Pat. No. 3,560,611; Ferrante, U.S. Pat. No. 4,255,256; Guirgis, U.S. Pat. No. 4,152,208; Furuta, U.S. Pat. No. 4,409,106; Goore, U.S. Pat. No. 3,800,035; Shepherd, U.S. Pat. No. 3,594,276; Kirkham, U.S. Pat. No. 3,635,798; Widmark, U.S. Pat. No. 3,700,555].

Kanter, U.S. Pat. No. 4,487,700, refers to a thixotropic barrier material of intermediate density to separate lymphocytes from erythrocytes and phagocytized leukocytes. Meyst, U.S. Pat. No. 4,283,289 refers to a leukocyte filter. The use of $NH_4Cl$ to lyse RBCs, while leaving most WBCs intact, is also known.

Hydroxyalkyl celluloses, and particularly hydroxyethyl cellulose, have been used as a thickening and stabilizing agent in pharmaceuticals and other compositions. However, they have never been used as sedimenting agents to separate lymphocytes from erythrocytes.

SUMMARY OF THE INVENTION

This invention relates to the use of hydroxyalkyl cellulose, particularly hydroxymethyl cellulose (HMC), hydroxyethyl cellulose (HEC) hydroxypropyl cellulose, (HPC), and hydroxybutyl methyl cellulose (HBMC) as sedimenting agents in blood cell separation. According to the present invention, about 80% intact leukocytes are recovered from the original number of leukocytes and over 95% of these remain in a viable state. Moreover, the erythrocytes which are separated into a lower phase, are also left intact.

The final concentration of HEC in the mixture is 0.05%, as compared to 3% HES in conventional separation methods. Accordingly, the harvested cells have relatively little HEC bound to them and may be washed off easily.

Unlike $NH_4Cl$ lysis, the HEC technique does not destroy granulocytes (granular leukocytes) or erythrocytes. Moreover, the WBCs recovered by this technique may be stored for at least one day without impairment of interferon production after exposure to an inducer.

DETAILED DESCRIPTION OF THE INVENTION

The present invention provides a particularly efficient agent for sedimenting intact leukocytes without destroying red blood cells present in the blood sample. In order that this invention may be more fully understood, we have set forth the following examples. These examples are for illustrative purposes, and are not to be construed as limiting this invention in any way.

EXAMPLE I

We pooled, mixed and sampled buffy coats (American Red Cross) and determined initial RBC and WBC counts using the Cell Dyn 400 cell counter (Sequoia International). We prepared a sedimenting agent by making a solution of 0.1% of HEC (w/v) and 0.9% of NaCl (w/v) in deionized water, stirring for at least one half hour until the HEC goes into solution. The sedimenting agent was slowly mixed with the buffy coat pool for at least one minute, poured into a separatory funnel, or other suitable vessel and allowed to settle for one and one-half to three (1.5–3) hours at room temperature or cooler. The final concentration of HEC in the mixture is preferably 0.05% (w/v). However, HEC may be present in a final concentration of between 0.025% and 0.5%.

After separation was completed we either drained the bottom RBC layer or aspirated the top WBC layer. The bottom layer could then be resedimented with fresh sedimenting agent to capture more WBCs, as previously described.

We tested the collected layers for RBC count, WBC count, WBC/RBC, and WBC viability (by Trypan blue exclusion test). Our results are set forth below:

| Sample | Vol. | $RBC*10^{12}$ | $WBC*10^{10}$ | WBC/RBC | Yield |
|---|---|---|---|---|---|
| Experiment 1476-19 (0.1% HEC, 0.9% NaCl stock solution) | | | | | |
| pool | 600 ml | 3.25 | 4.00 | 0.01 | 100% |
| top layer | 720 ml | 0.20 | 3.37 | 0.17 | 84% |
| bottom | 500 ml | 2.73 | 0.34 | 0.001 | 9% |
| top layer (after wash) | 160 ml | — | 3.12 | — | 78% |
| Experiment 1476-7 (0.1% HEC, 0.9% NaCl stock solution) | | | | | |
| pool | 1000 ml | 5.88 | 4.66 | 0.01 | 100% |
| top layer | 830 ml | 0.11 | 3.72 | 0.34 | 80% |
| bottom | 1190 ml | 5.45 | 1.09 | 0.002 | 23% |
| top layer (after wash) | 130 ml | 0.07 | 3.58 | 0.51 | 77% |

We washed the harvested cells using centrifugation. The cells may alternatively be cleaned by using tangential flow filtration or other conventional methods.

The WBC layer was spun at $100 \times g$ for 7 minutes. We discarded the supernatant and resuspended the pellet in leukocyte medium at 37° C. and counted the WBC. We added the WBCs to a 2 liter volume of MEM medium, human serum, and alpha interferon primer at a concentration of $1 \times 10^7$ WBCs/ml. Induction took place in 6 liter round bottom flasks maintained in 37° C. water baths.

After an initial incubation period of 3 hours, we added Sendai virus to the flasks in order to induce alpha interferon production. The induction period was typically 18 hours. Alpha interferon was then collected by centrifugation at 4000 g's for 20 minutes. Samples of the supernatant were submitted for CPE (cytopathic effect) assay.

The CPE assay is based on the ability of alpha interferon to protect certain cells against certain viruses. In the assay used, Hep 2 cells were grown to confluence in 96 well microtiter plates. Serial dilutions of the alpha interferon were added to the sample wells and incubated with the cells (37° C., 5% $CO_2$) for about 20 hours. Next, VSV virus was added to the wells to infect unprotected cells. After an incubation period sufficient to achieve 100% cell death in the control wells (i.e., only cells and virus present in these wells), all wells were stained with Gentian stain. Intact cells appear purple due to the membrane picking up the stain. The well number (i.e., the dilution) at which 50% of the cells had been protected is called the endpoint. The endpoint was then used to correlate the titer of the sample (in units of interferon/ml.) to standards from the NIH.

When a stock solution of 0.05% HEC was used for cell separation, a very slow separation occurred. That is, when compared with separations using 0.1 and 0.2% HEC stock solutions, the 0.05% HEC separation had not proceeded as far as the latter two, in a comparable time period. Also, the 0.05% separation seemed to have more RBC contamination in the middle layer (as evidenced by a pink band rather than the white one seen in each of the other separations).

A stock solution of 0.5% HEC did not give a good separation—only two layers formed and more WBCs were recovered from the bottom layer than from the top layer. Also, the "purity" of the top layer, as expressed in terms of WBC/RBC, was less than ½ of that seen in the combined two upper layers of the 0.1% HEC separation (i.e., 0.14 compared to 0.30). Concentrations of 0.7 and 1.0% HEC were even less effective.

Over a series of experiments, we obtained alpha interferon titers in the range of 20–50,000 Units/ml.

We prepared a cytospin smear of HEC-collected WBCs. We treated the cells with MAY-GRUNWALD-GIEMSA stain, and inspected the cells microscopically. A cell differential study showed the leukocyte subpopulations to have essentially the same distribution as in the original blood pool. The morphology of the leukocytes was normal.

EXAMPLE II

We prepared a 0.1% solution of hydroxypropyl cellulose (300,000 m.w.; Aldrich Chemical) as described for HEC in Example I, above. The 0.1% HPC/0.9% NaCl solution was mixed with an equal volume of buffy coat pool. In two separate experiments, we observed good separation between WBCs and RBCs. However, because neither separation had been done in a separatory funnel, it was difficult to effectively collect the top layer without contaminating it with RBCs from the bottom layer.

We conducted the same type of experiments with hydroxybutyl methyl cellulose (HBMC). Using the same 0.1% concentration of polymer with 0.9% NaCl, the separation appeared to occur faster and looked better than a concurrently run HEC separation.

While we have hereinbefore presented a number of embodiments of this invention, it is apparent that our basic method can be altered to provide other embodiments which utilize the process of this invention. For example, the WBC yield may be increased by various means. First, sedimentation may be carried out in a device facilitating RBC/WBC separation. This would include a device having a constriction at the expected location of the RBC/WBC interface, or one having draining or aspirating means designed to minimize agitation of the interface. Second, a thixotropic agent may be added. Such an agent should be selected so that its specific gravity would cause it to collect into a barrier structure separating the RBC and WBC layers. Third, the extraction step could be repeated as desired with fresh sedimenting agent.

Other hydroxyalkyl cellulose could be substituted for HEC and HPC, as sedimenting agents.

In addition to unit gravity sedimentation, HEC might also be used in RBC/WBC separation by centrifugation. HEC may be used in the separation of cells from cell debris. Finally, the WBCs and RBCs provided by the present technique may be separated into WBC or RBC subtypes or fractionated to yield various WBC or RBC constituents.

The scope of this invention is to be defined by the claims appended hereto rather than by the specific embodiments which have been presented hereinbefore by way of example.

I claim:

1. A method of separating leukocyte and erythrocyte-containing blood or blood fraction into a first fraction enriched for leukocytes in which over 80% of the original leukocytes are recovered and a second fraction enriched for erythrocytes, which method comprises mixing the blood or blood fraction with a sedimenting agent consisting essentially of a hydroxyalkyl cellulose, permitting the mixture to settle and separating the mixture into said first and second fractions.

2. The method of claim 1 in which the settling occurs at unit gravity.

3. The method of claim 1 in which the final concentration of hydroxyalkyl cellulose in the mixture is 0.025% to 0.5%.

4. The method of claim 1 in which the hydroxyalkyl cellulose is hydroxyethyl cellulose.

5. The method of claim 1 in which the hydroxyalkyl cellulose is hydroxypropyl cellulose.

6. The method of claim 1 further comprising use of a thixotropic barrier material to separate the first and second fractions.

7. The method of claim 1, which does not comprise exposure of the cells to conditions which destroy erythrocytes or granulocytes.

8. The method of claim 1 in which the hydroxyalkyl cellulose is hydroxymethyl cellulose.

9. A method of obtaining leukocyte cells suitable for interferon induction which comprises providing blood or a leukocyte-containing fraction of blood, mixing the blood with a sedimenting agent consisting essentially of a hydroxyalkyl cellulose, so as to leave an upper layer enriched in leukocytes, in which over 80% of the original leukocytes are recovered, and recovering leukocytes from said upper layer which are suitable for interferon induction.

10. The method of claim 9 in which the leukocytes are suitable for interferon induction even after a day of storage.

11. The method of claim 9 in which the hydroxyalkyl cellulose is selected from the group consisting of hydroxymethyl, hydroxyethyl, hydroxypropyl and hydroxybutyl methyl celluloses.

12. The method of claim 10 in which the hydroxyalkyl cellulose is selected from the group consisting of hydroxymethyl, hydroxyethyl, hydroxypropyl and hydroxybutyl methyl celluloses.

* * * * *